United States Patent
Mouche et al.

[11] Patent Number: 5,360,549
[45] Date of Patent: Nov. 1, 1994

[54] FEED BACK CONTROL DEPOSIT INHIBITOR DOSAGE OPTIMIZATION SYSTEM

[75] Inventors: Richard J. Mouche; Thomas F. Droege, both of Batavia, Ill.

[73] Assignee: Nalco Chemical Company, Naperville, Ill.

[21] Appl. No.: 53,105

[22] Filed: Apr. 27, 1993

[51] Int. Cl.$^5$ .................................. C02F 5/08
[52] U.S. Cl. ........................... 210/696; 210/742; 210/101; 210/143; 210/149; 364/500
[58] Field of Search ............... 210/696–701, 210/742, 746, 101, 143, 149, 167; 364/500

[56] References Cited

U.S. PATENT DOCUMENTS

| | | | |
|---|---|---|---|
| 4,648,043 | 3/1987 | O'Leary | 210/143 |
| 5,171,450 | 12/1992 | Hoots | 210/701 |
| 5,174,654 | 12/1992 | Droege | 374/7 |
| 5,185,533 | 2/1993 | Banks et al. | 250/575 |
| 5,248,198 | 9/1993 | Droege | 374/7 |

*Primary Examiner*—Peter A. Hruskoci
*Attorney, Agent, or Firm*—Dorn, McEachran, Jambor & Keating

[57] ABSTRACT

A method of and a system for monitoring circulating water systems for conditions susceptible to deposition of a variety of scaling deposits. The invention includes presenting upset conditions at a surface area in the circulating water stream, or in a sidestream in a conduit connected to the main circulating water system, and closely monitoring either heat transfer rate or heat transfer resistance at the water contact surface adjacent the area of upset. When conditions for scaling are present, the upset conditions tend to cause formation of scale deposits at the upset area before the scaling occurs in the main circulating water stream, permitting countermeasures to be taken which inhibit scaling. In the specific case of boilers, heat exchangers or cooling towers, $CaCO_3$ scaling is monitored at an area where the upset conditions are present, the upset conditions are an increase in the heat transfer rate. The solubility of $CaCO_3$ being inversely proportional to temperature, an increased heat transfer rate causes scaling which is monitored first at the upset area, and the presence of $CaCO_3$ in the water stream is counteracted by automatic increase in the amount of scaling inhibitor pumped into the system.

24 Claims, 5 Drawing Sheets

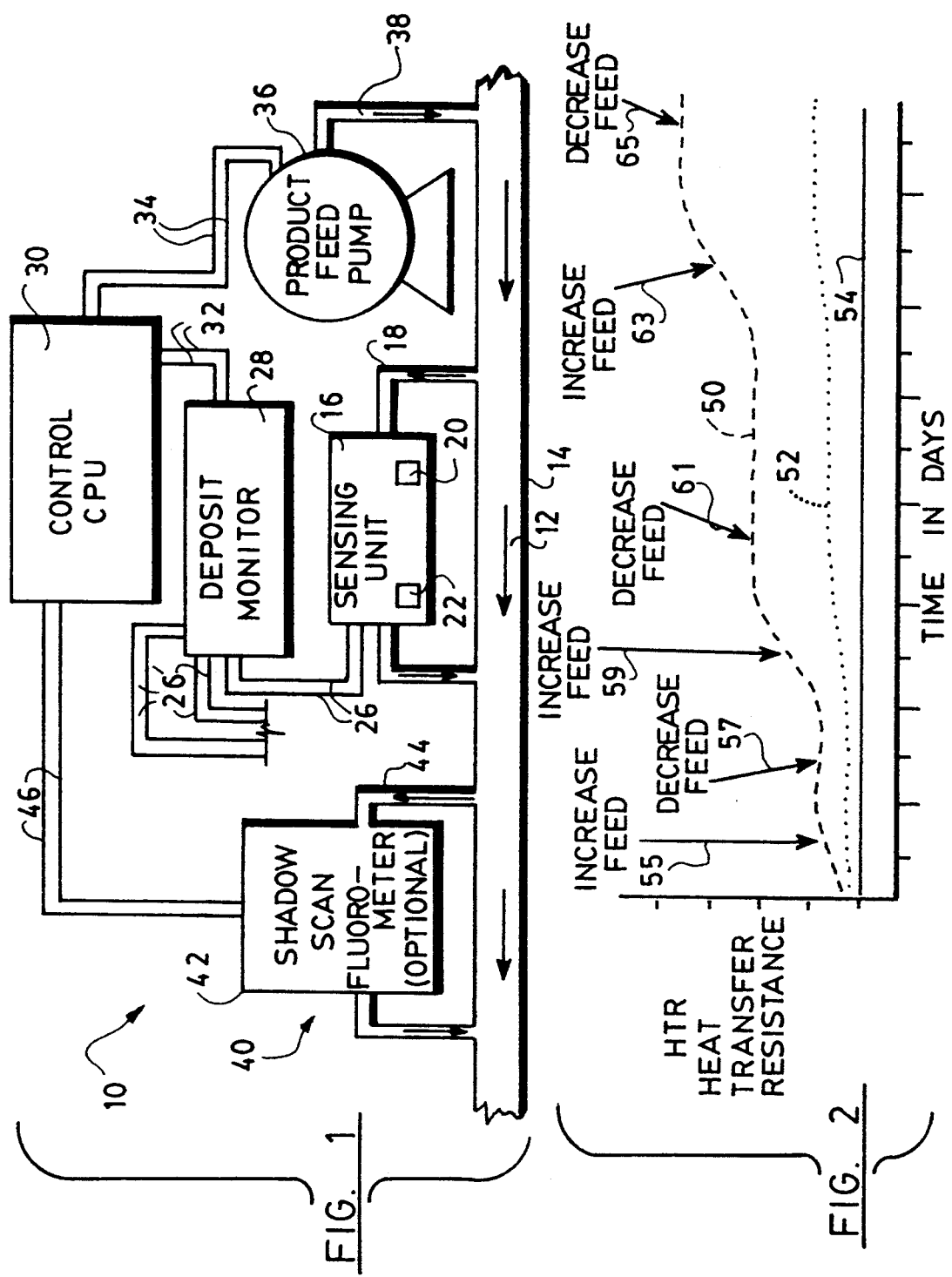

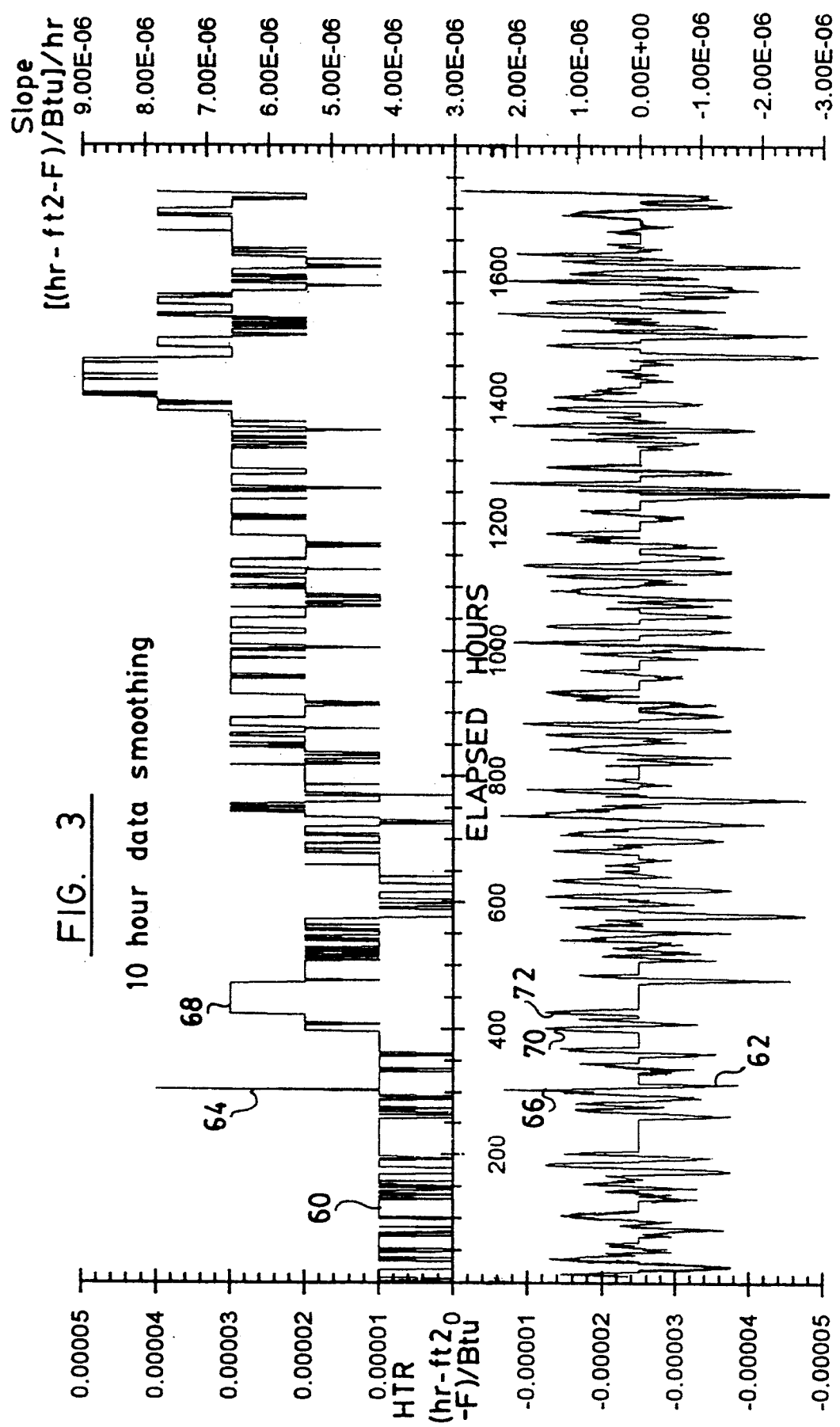

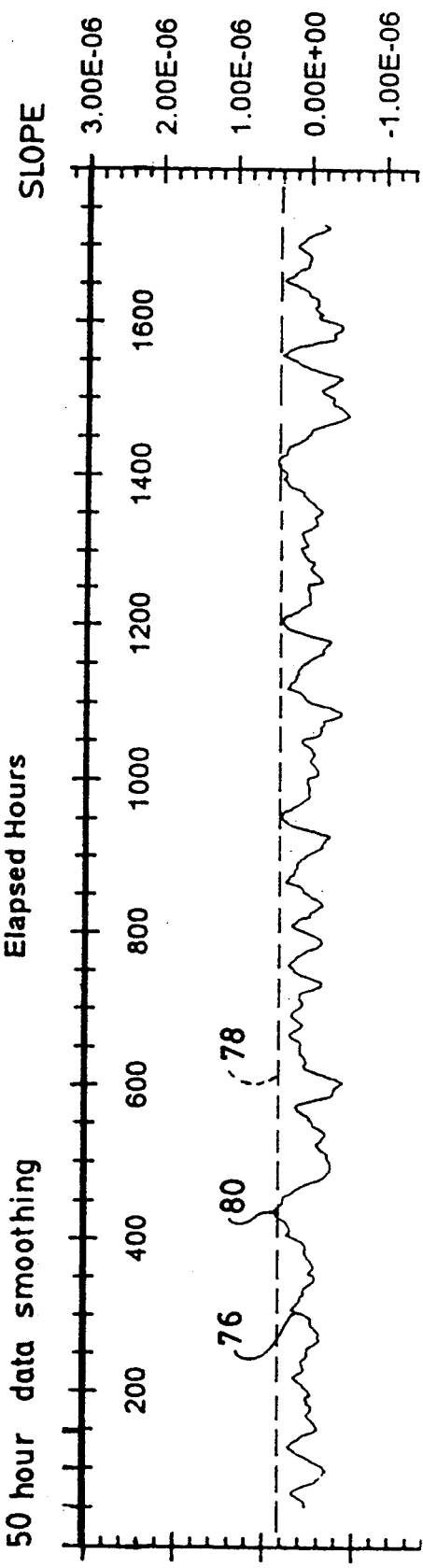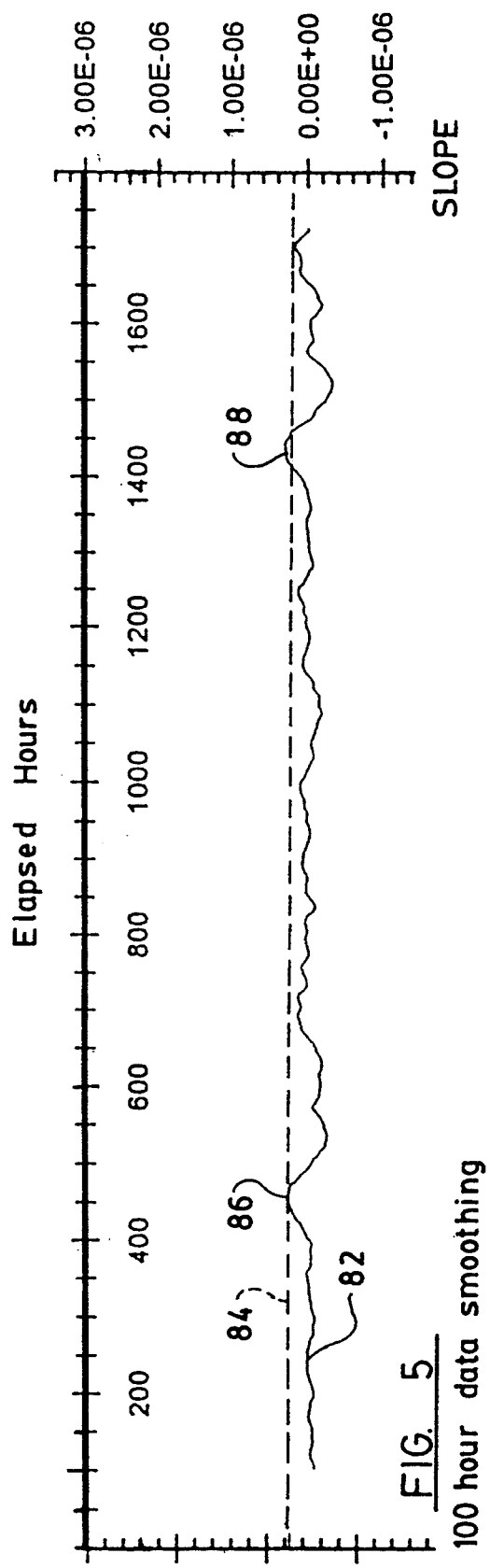

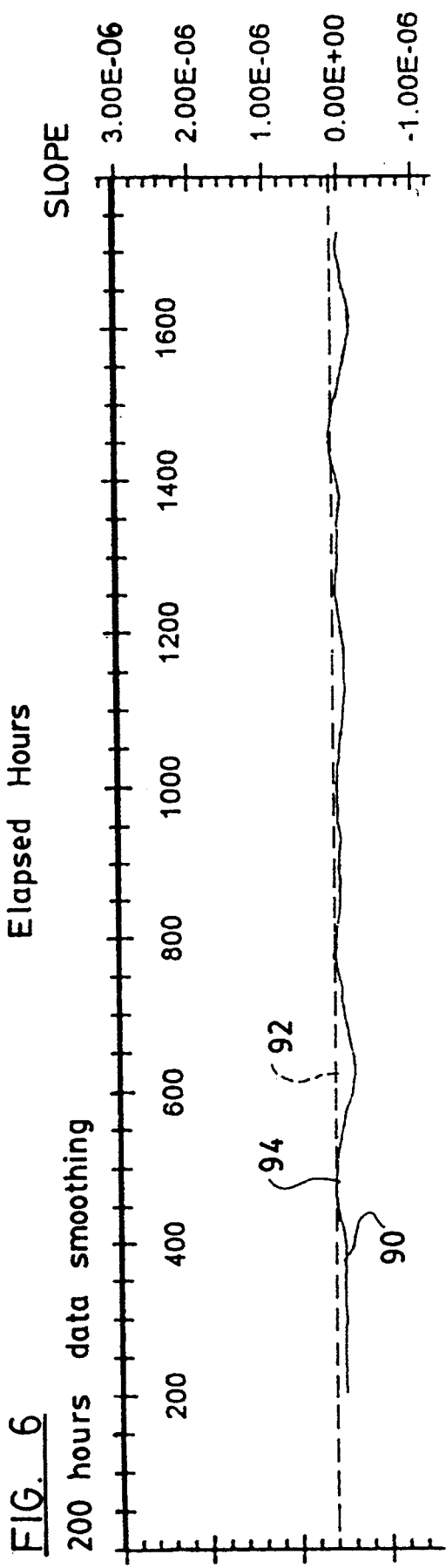

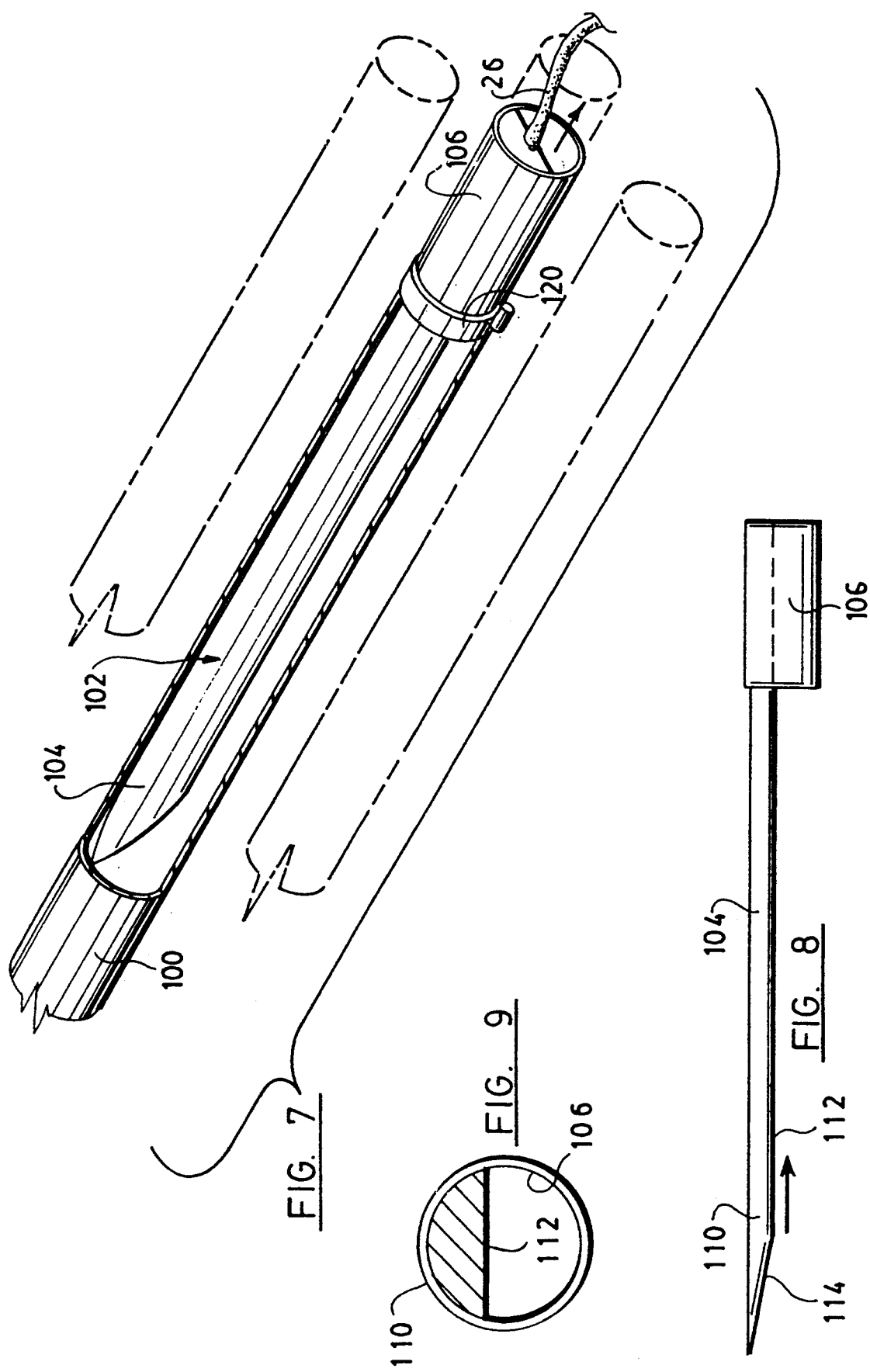

FEED BACK CONTROL DEPOSIT INHIBITOR DOSAGE OPTIMIZATION SYSTEM

BACKGROUND OF THE INVENTION

1. Field of the Invention

This invention relates generally to the prevention of deposits on equipment employed in a circulating water system such as heat exchangers and boilers. The deposit may be an inorganic scale (e.g. calcium carbonate in a boiler condenser) or it may be an organic biofilm such as algae or bacterial growth, entrained in a source of natural water. More specifically, this invention relates to a method and system for monitoring a circulating water system so as to provide an indication of the amount and of the need to add a counteracting agent to the circulating water system.

2. Background Art

Control of deposits on the walls of heat-exchanging water circulating equipment is important for many reasons. It is sufficient to call to mind that the deposit can cause turbulence, meaning both inefficient flow and an increase on pump demand, or it can reduce heat transfer which means reduced efficiency in a heat exchanger.

Consequently, deposit inhibitors are introduced into the water entering the circulating system. In the case of inorganics ($CaCO_3$, $MgCO_3$, etc.), so-called water softeners (scale inhibitors) are used as the treatment, stopping formation of the scale by neutralizing the offending ions; in the case of biofilms, biocides are used to destroy kill and prevent growth of microorganisms. The term "deposit inhibitor" is here used in an eliminative sense: addition of chemical "product", added to the stream of water, either to eliminate (prevent) inorganic ions from participating in scale formation or to eliminate (preclude) biofilms by destruction or prevention of the organic body.

Because the chemistry of the deposits can vary so widely, the inhibitor may take other forms besides a water softener or a biocide. Acid or alkaline treatment may be employed to adjust pH. Indeed, the treatments (inhibitors) fall into major classifications: threshold inhibitors, dispersants, surfactants and crystal modifiers, as explained in *The Nalco Water Handbook*, Second Edition, McGraw-Hill, 1988. The present invention is not restricted to any particular deposit former or inhibitor feed product.

It is consequently customary to employ some means to determine if a deposit of a particular kind has formed to any appreciable extent on the walls of the equipment in contact with the moving or circulating body of water.

It has been proposed to determine the extent of deposit buildup by mimicking, as much as possible, the conditions in a system for which fouling is being monitored. The method includes the steps of withdrawing a continuous sample of the system water in a side stream tube or conduit, monitoring the flow rate of the sample, waiting for a steady state or equilibrium condition to be achieved, and measuring the heat transfer resistance across the wall thickness of the sampling tube. After a reference heat transfer rate, or the tube wall temperature is established, upset conditions are introduced into the system. These include changing the heat transfer rate and decreasing the flow rate of the sample water in the system, until fouling occurs. Fouling generally affects the operating conditions of the monitor. For example, if the heat transfer rate is being held constant, then fouling causes a decrease in temperature. Conversely, if the tube wall temperature is held constant, then an increase in heat transfer rate is required to maintain the constant temperature.

The method is described in an article entitled "Cooling Water Fouling Monitor Series Upsets, Evaluates Changes" appearing in *Chemical Processing*, April 1990, pp. 34–38. As is stated in the article, the known monitor and method is "very useful for tracking fouling rate variation resulting from system upsets and changes in treatment program and flow rate. Nevertheless, the method and monitor is most sensitive to dramatic upsets, such as when there is an acid overfeed, and is much less sensitive to gradual scaling occurring over long periods of time, often weeks or months. The method also requires close monitoring of the flow rate within the sidestream tube or conduit. Another drawback is that the described method requires compensation of upset conditions by manual control over the addition of product to check the effects of the upset conditions.

The known system has heretofore achieved certain benefits which, though useful, are subject to other disadvantages. The known system monitors that a deposit is in fact occurring or has already occurred. However, monitoring of a deposit which has already occurred may be unacceptable in certain applications. In most cases, a determination that an unwashed deposition has occurred on a pipe wall of a condenser or heat exchanger system comes too late to prevent deterioration of system operation. Reversing the effects of such deposition often requires system shutdown and either replacement of the system elements, such as pipes, or cleaning of the system by acidic agents. Either of these alternatives is undesirable from a standpoint of cost and efficiency and may also cause unwanted effects on the system hardware. For example, excessive or repeated cleaning also causes damage to the system elements.

Thus, what is necessary, is a monitoring and anti-fouling system which can anticipate formation of deposits in an operating system before they occur and to simultaneously counteract the conditions which can lead to fouling of the system well before deposits begin forming on the walls. An automatic compensating mechanism which is sensitive to both drastic upset conditions in the circulating water system and to deposits occurring over great periods of time is also desirable. Ideally, such an automatic compensating mechanism will automatically feed product into the circulating water system to compensate for both system upset conditions and gradual deterioration caused by continuous deposits at a time immediately upon sensing by the monitor of a predetermined set of characteristics indicative of either of the two upset condition or gradual scaling condition. Most preferably, the monitor and method sense these characteristics well before they occur in the circulating water system itself, and the automatic product feed mechanism is triggered before the undesirable conditions are permitted to cause damage to the system elements.

SUMMARY OF THE INVENTION

Accordingly, an objective is to apply heat by a heating element to induce deposit formation in the sample line or bypass in such a manner that deposition of the scale or biofilm can be interdicted before it starts. Another object of the present invention is to employ a thermistor in combination with the heating element to generate a control signal which increases the pumping rate of the deposit inhibitor when the thermistor senses the occurrence of an unacceptable deposit thickness in the sample line.

To achieve these objectives we depend on the principle that the deposition of scale formers and biofilm formers is a function of temperature. The deposition of calcium carbonate for example increases.

Accordingly, this invention provides a method of correcting for scale deposit on the inside walls of a water container through which water in a circulating water system is flowing at a predetermined temperature comprising the steps of providing at least one sensing unit for sensing heat transfer rate or heat transfer resistance through a contact surface which is in contact with the water in the circulating water system, providing a deposit monitor station for monitoring heat transfer rate or heat transfer resistance and an electrical connection between the one sensing unit and the deposit monitor, providing at one area adjacent to the contact surface a first temperature modulator to maintain that area at a temperature which stimulates scale deposit of the scale former on the contact surface, periodically monitoring the sensing unit by measuring at predetermined time intervals the heat transfer rate or heat transfer resistance being sensed by the one sensing unit, generating an electrical signal corresponding to the heat transfer rate or heat transfer resistance which is sensed and transmitting the electrical signal to the deposit monitoring station, recording the signal received by the monitoring station and analyzing the data signal record to determine whether predetermined parameters indicative of specific conditions of the water in the circulating water system have been met, and upon a determination of the parameters having been met, calculating a dosage of scale inhibitor determined sufficient to inhibit further formation of scale deposit upon the contact surface and imparting into the circulating water system the calculated dosage of scale inhibitor deemed sufficient to inhibit further formation of scale deposit on the contact surface as well as on the inside walls of the water container.

This invention also provides a system for correcting for scale deposit on the inside walls of a water container containing a circulating water system through which water is circulating at a predetermined temperature, the system comprising at least one sensing unit for sensing heat transfer rate or heat transfer resistance through a contact surface which is in contact with the water in the circulating water system, a deposit monitor station for monitoring heat transfer rate or heat transfer resistance and an electrical connection between the one sensing unit and the deposit monitor, a first temperature modulator disposed at one area adjacent to the contact surface for maintaining that area at a temperature which stimulates scale deposit of the scale former on the contact surface, a recording means for recording the data signal received by the monitoring station, a data processor for analyzing the data signal record to determine whether predetermined parameters indicative of specific conditions present in the water of the circulating water system have been met and for calculating a dosage of scale inhibitor determined sufficient to inhibit further formation of scale deposit upon the contact surface, and a scaling inhibitor feed means for transmitting an activation signal which causes imparting into the recirculating water system the calculated dosage of scale inhibitor deemed sufficient to inhibit further formation of scale deposit on said surface as well as on the inside walls of said water container upon a determination of the parameters having been met.

BRIEF DESCRIPTION OF THE DRAWINGS

FIG. 1 illustrates a schematic diagram of the components according to the present invention;

FIG. 2 is a plot of heat transfer resistance of the monitoring data of plural sensing units at different heat transfer rates taken over the course of a number of days;

FIGS. 3-6 are plots illustrating methods and techniques of analysis of the data received from sensing units;

FIG. 7 illustrates, in a perspective view, a partial cutaway view of another embodiment of a sensing unit according to the present invention;

FIG. 8 is an elevation view of the sensing unit shown in FIG. 7; and

FIG. 9 is a side elevational view of the sensing unit shown in FIG. 8.

DETAILED DESCRIPTION OF THE PREFERRED EMBODIMENTS

FIG. 1 illustrates in a schematic diagram a system according to present invention, designated generally at 10. The system 10 monitors a circulating water system, such as a heat exchanger, boiler, condenser and the like, in which it is important that heat transfer occur quickly, efficiently, and with as little impediment to the heat transfer through the system walls as possible. For example, as shown in FIG. 1, the circulating water system is represented by a tube 12 having tube walls 14 through which heat must be transferred. Water circulates through the tube 12 in the direction of the arrows. The tube 12 may be a heat exchanger or condenser in an electrical power utility's generating plant, and steam condenses at a cooling station outside the tubing after the steam has passed through a power turbine. The steam gives off heat in condensing, which heat must be removed to maintain the temperature of the cooling station at a level where steam continues to condense. These cooling stations are generally open to the environment, and even though the circulating water system is generally closed, evaporation of water into the environment is to be expected. Cooling towers or cooling ponds are used to evaporate the water.

One consequence of evaporation of great amounts of water is a buildup in salts and impurities in the water remaining. Evaporation removes only water from the system, since salts and impurities have a higher vapor pressure and are too heavy to evaporate with the water. Removal of the salts and impurities is done by a process called blowdown. Monitoring of the solution concentration of the water in the cooling tower basin or cooling pond, or alternatively, upon a determination that a specific event, such as time elapse, has occurred, triggers a mechanism for blowdown of the water in the basin. The blowdown removes the dissolved salts and impurities together with a certain amount of water. The makeup water quantity is thus the sum of the blowdown and all of the water which has evaporated as vapor.

All water which has evaporated or any blowdown water removed from the system must be replaced by fresh water brought in from outside the system. Ideally, this water is free of impurities such as salts or microbiologic contaminants. However, when fresh water requirements are great, as in the case of public utility power generating plants, the expense of pure or distilled water is prohibitive. Accordingly, some method of treatment of relatively clean water, which nevertheless contains various salts or microbiological agents, must be found to overcome the tendency of these impurities to deposit or scale onto the inside of walls 14 of the system tubing 12.

The water circulating in the circulating water system generally is required to have specific predetermined characteristics, such as a certain pH range, etc. For example, an electric generating plant may have an automated system for pH control which monitors the pH. When the pH is out of the specified range, a correction is automatically made by addition of an acidic or basic compound to bring the pH into the specified range. Other corrections for system conditions may be made as a complement to a monitor for those conditions. Many of these types of systems can easily correct for the conditions because there is a direct correspondence between the monitoring mechanism and the amount of correction needed.

In the case of scale deposits, however, the monitoring equipment heretofore available has not been consistently accurate enough to enable precise correction of conditions apparently found in the circulating water stream. One indicator of scaling or other deposits used in the past has been the heat transfer rate, and the resistance to heat transfer, through the tube wall of a circulating water system. As the tube builds up scale deposits along the wall, the heat transfer rate decreases, making the heat exchanger system less efficient. As the heat transfer rate decreases because of the heat transfer resistance presented by the scaling deposits, a direct relationship is considered to exist between the amount of scaling and the heat transfer resistance.

As noted above, one problem with direct measurement of heat transfer resistance is the lack of consistently precise readings of heat transfer rate and heat transfer resistance. One attempt at solving this problem was addressed by Brindak in U.S. Pat. No. 4,346,587, now the subject of reissued Patent No. Re. 33,468. Brindak proposed providing a mobile test apparatus including a heat transfer test assembly, but the testing for fouling disclosed therein is dependent on a knowledge of the fluid flow velocity and the testing also depends on thermocouples for measuring tube wall temperatures. Moreover, there is no provision for anticipating fouling which is expected to result, and cannot provide anti-fouling measures before fouling occurs in the system plant. The cooling water fouling monitor described in the aforementioned article in *Chemical Processing*, also does not provide a capability of anticipating fouling which has not yet deteriorated the main plant, but is able to counteract severe upset conditions.

The inventive device relies upon an improved deposit monitor sensing unit 16 which provides greater sensitivity to changes in both the temperature and in heat transfer resistance. Such a sensing unit is described in U.S. Pat. No. 5,174,654 which issued Dec. 29, 1992 to a co-inventor of the present invention. The subject matter of U.S. Pat. No. 5,174,654 is incorporated by reference herein. A sensing unit 16, such as one made according to U.S. Pat. No. 5,174,654, is clamped onto test tube 18 through which flows a side stream of the main system circulating water flowing through tube 12. The preferred heat sensing unit 16 provides accurate and precise readings of heat transfer rate and heat transfer resistance. These readings can be derived independent of the amount or rate of water flow in either the main system tube 12 or the sidestream test tube 18.

An advantage which derives from use of a sensing unit 16 according to U.S. Pat. No. 5,174,654 is the ability to take readings at two or more different externally applied temperatures so that the heat transfer rate is different at different points in the sensing unit. The advantage derives from the setting of different upset conditions, such as increased temperature, which causes premature fouling at the upset condition station but does not cause fouling at the normal condition station.

For example, for the case of two separate reading stations 20,22 contained in unit 16, the heat transfer rate can be set differently for station 20, e.g. 30,000 BTU ft.$^2$/hr., and for station 22 at 35,000 BTU ft.$^2$/hr. This is possible by simply applying a greater amount of heat to the block with the higher heat transfer rate.

As an example of a higher heat transfer rate upset condition, the case of calcium carbonate ($CaCO_3$) which has been noted as a major cause of boiler or condenser scale when hard water is used in heating or condenser systems. To counteract the formation of scale, an antifoulant or scaling inhibitor product which in the case of $CaCO_3$ is some type of water softener of varying composition, is fed to the circulating water stream upstream of the water monitor. The scaling inhibitor product inhibits formation of scale at the more sensitive heat transfer station. $CaCO_3$ has a rate of scaling that increases with increasing temperature. This characteristic is contrary to most salts, which dissolve faster with increasing temperature. Thus, the higher heat transfer rate station e.g. 20, is the one undergoing the upset condition, and scaling will begin first.

Referring again to FIG. 1, the sensing unit 16 is electrically connected by means of electrical leads 26 to a deposit monitor 28. Other sensing units, not shown, also may be connected by electrical leads 26' to the deposit monitor 28. Use of several sensing units may be desirable where a circulating water system has a number of critically sensitive areas where scaling may need to be monitored. For example, in a power generating plant, a deposit monitor 28 may be connected to one or more sensing units 16 at a condenser (or condensers) and other sensing units (not shown) may be disposed at a boiler plant of the same circulating water system, being connected to the deposit monitor 28 by electrical leads 26'.

The deposit monitor 28 is illustrated as being connected to a control central processing unit (CPU) 30 by electrical leads 32. Alternatively, the CPU 30 may be integral with the deposit monitor 28, that is, one integrated analysis control system may provide all of the functions provided by the two separate units.

The control CPU 30 receives the signals from the deposit monitor 28 which provide an indication of the amount of scaling, and more importantly, the rate of scaling, which is occurring in the test tube 18. Predetermined parameters may be set in the CPU 30 taking into account known characteristics of the circulating water, the types and amounts of deposits and impurities which are expected in the water and of the circulating water system. For example, if the rate of scaling at one sensing station 20,22 exceeds a certain predetermined rate, then the CPU 30 control may set in motion a chain of events to correct for the specific condition monitored which is causing the increased rate of scaling.

The control CPU 30 is electrically connected, by a set of electrical leads 34, to a means of feeding inhibitor product, such as a product feed pump 36. The product feed pump 36 is in fluid communication with the circulating water system in tube 12 by a feed tube 38. Generally, the feed pump 36 feeds inhibitor product through tube 38 directly into the circulating water at a point upstream of the position where tube 18 and sensing unit 16 connect to the fluid stream. This disposition provides at least two advantages in that any indication of scaling or deposit is immediately counteracted by an increase in the inhibitor product feed rate pumped from the pump 36 at a point before the circulating water enters the system and thus inhibiting scale formation at the soonest possible time and as soon as possible after the sensing unit has triggered the mechanism for product feed. Moreover, increase in the inhibitor product feed rate upstream of sensing unit permits the deposit monitor 28 and CPU 30 to immediately evaluate the effect of the additional inhibitor product on the scaling rate. Thus, if the scaling continues. then additional product feed may be immediately called for and the CPU 30 continues the response by signalling the pump 36 to provide a still higher rate of inhibitor product to the circulating water stream in tube 12.

Illustrated in the schematic diagram of FIG. 1 is an optional mechanism 40 for monitoring the exact level of product which is present in the circulating product stream. The mechanism 40 is preferably a ShadowScan (TM) Fluorometer 42 which is available from Nalco Chemical Company of Naperville, Ill. The mechanism 40 is also the subject of U.S. Pat. Nos. 4,992,380, 5,171,450, and 5,185,533, assigned to a common assignee with the present invention. The subject matter of each of these patents is incorporated by reference herein.

The mechanism 40 preferably comprises a fluorometer 42 to which monitors a sidestream tube 44 that withdraws a continuous sample of the circulating water from tube 12, much like tube 18 does for the sensing unit 16. The fluorometer 42 is electrically connected by leads 46 to the control CPU 30, and provides precise and accurate indication of the level of the product which is present in the circulating water in tube 12. The CPU may incorporate the level of known scale inhibitor product into the calculations which are necessary to provide the optimum level of product to the circulating water stream. Disposing the mechanism 40 downstream of the product feed pump 36 also provides a direct indication of whether sufficient scale inhibitor product is being pumped into the tube 12 to inhibit any scaling which is sensed by the deposit monitor 28. A fail safe mechanism is also provided by the fluorometer because an indication that not enough product is being pumped by pump 36 into the fluid stream. The indication will set off a trigger within the system which will provide an alarm to the system operator of a failure or need to investigate the scaling inhibitor mechanism 10.

Illustrated in FIG. 2 is a plot of heat transfer resistance in a number of sensing units at different upset conditions. The plot of heat transfer resistance is taken over a number of days, and represents data of a monitoring process of a scale deposit of a compound which has an inverse solubility with increasing temperature, such as calcium carbonate. Continuous readings may be taken at successive periods of a predetermined duration. For example, two readings per hour taken at half hour intervals may be required for a mechanism having a sufficiently quick response to upset conditions. Nevertheless, a steady equilibrium state in heat transfer rate is practically difficult, if not impossible, to achieve and noise, in the form of sudden changes in measured heat transfer rate, are common. Thus, measured data must be averaged over a longer time period by utilizing specific parameters, as will be explained below.

Referring again to FIG. 2, the heat transfer resistance is plotted against time (in days) and provides three different curves, one each for different heat transfer rates. For the example of monitoring calcium carbonate, a curve 50 shows the heat transfer resistance taken at a higher temperature, e.g. at a heat transfer rate of 35,000 BTU ft.$^2$/hr. A second curve 52 may represent measurements at a sensing unit having an intermediate heat transfer rate of 32,000 BTU ft.$^2$/hr. and a third curve 54 may represent measurements at a sensing unit which does not heat the unit at all, but provides readings at a temperature equal to the circulating water temperature of the heat exchanger as embodied in the tube 12. Because calcium carbonate has an increasing solubility with increasing temperature, greater scaling occurs at the higher temperature sensors, and the heat transfer resistance subsequently increases, as shown in the curve 50. To some extent, the increases in heat transfer resistance of the intermediate curve 52 mirrors, albeit to a much lesser extent, the increases shown in curve 50. Ideally, the curve 54, at the lowest temperature, will be flat to indicate no scaling in the sensing unit reflecting the actual heat condenser temperature conditions.

Using curve 50 as the "leading indicator" of conditions which will precipitate the calcium carbonate and form scaling, the mechanism automatically triggers an increase in product feed from the pump when the increase in heat transfer resistance achieves a predetermined rate, or alternatively or in addition to, the heat transfer resistance (HTR) rate increase is consistently above a specified predetermined rate. The increase in product feed is begun at a point designated 55 on the curve 54 and has the immediately discernible effect of making the rate of HTR stop increasing, i.e. the curve 54 becomes flat. After the stability of HTR is verified for a long enough time, the product feed is decreased at 57 to the level which may correspond to the level before the increased feed.

After the system 10 again reaches an equilibrium steady state, an upset condition may occur which requires the immediate and drastic increase in product feed which may be necessary to counteract a severe upset condition which is indicated by a steep increase in the HTR. As soon as the conditions are noted, the increase product feed begins at 59 and continues for a sufficient length of time until the curve 54 becomes flat for long enough to again trigger a decrease in product feed rate 61. The process is repeated, as at 63,65, as often as is necessary to inhibit scaling yet optimizing the use of product.

The trigger rates and specific parameters which indicate specific conditions which require additional product feed can be programmed into the control CPU by a person of ordinary skill in the art. Adjustments of the rate of duration of rate, or of other factors which trigger the addition of more product feed or amount of sole inhibitor product which must be added to the circulating water stream, as will be explained below.

Curve 52 or other intermediate temperature curves may be monitored by the deposit monitor 28 and may be analyzed by the CPU 30 (FIG. 1). These curves 52,54 are considered optional but may be necessary in applications where severe upsets in the system are to be minimized as much as possible. For example, electric utilities desire to minimize downtime of the electricity generating plant. Thus, any upset condition which is anticipated by the backup system provided by other sensors, the data of which is set forth in curves 52, 54, will allow the normalization of plant operation before the plant is severely damaged. The quicker the normalization, the less damage and ergo, the less a plant would require shutdown for repairs or for refurbishing equipment.

The secondary indication curves 52,54 act as backup to the monitoring of the principal curve 50 in two ways. First, if scaling is occurring because of an unexpected phenomenon, the scaling may be first indicated at a sensing unit having a different temperature. For example, if the mechanism 10 is intended to inhibit scaling of calcium carbonate, another salt which does not have an inverse solubility with increasing temperature would indicate scaling at a lower temperature first. Should such compound be inadvertently introduced into the system, the lower temperature sensors would first indicate the presence of an unwanted condition in the system. Thus, the CPU (FIG. 1) would be programmed to monitor all of the curves for changes in predetermined indicators, so as to trigger corrective addition of the scaling inhibitor or an alarm should unrecognizable conditions be encountered.

Secondly, monitoring a sensing unit under conditions which are identical to the circulating water in the heat exchanger allows for the creation of a historical record of the specific amount of scaling which has already occurred in the plant. An indication of heat transfer resistance beyond a specified predetermined level indicates the need to clean the plant hardware so as to remove scale deposits and thereby increase heat exchange efficiency.

FIGS. 3–6 illustrate the effective analysis in a device according to the present invention which provides the necessary indications for feeding additional scale deposit to a circulating water system. FIG. 3 is a composite graph, the top portion of which plots a curve 60 that corresponds to the heat transfer resistance (HTR) measured in $(hr\text{-}ft^2\text{-}°f.)/Btu$ plotted over a long time, in this case over 1700 hours. The bottom portion of FIG. 3 shows the slope of curve 60 which has been calculated by taking the average of the previous 10 hours ("10 hour data smoothing) so as to remove the effects of temporary spikes or troughs which may be caused by spurious or instantaneously aberrant readings. The units at the left ordinate axis are in hours and the units on the left coordinate axis correspond to HTR shown in the top portion of FIG. 3. The units of the bottom portion of FIG. 3 correspond to the slope, having units $[(hr\text{-}ft^2\text{-}°F.)/Btu]/hr.$, and are shown in the coordinate axis on the right side of FIG. 3. The top portion and bottom portion of FIG. 3 corresponds to the readings taken at the same particular time.

The bottom portion of FIG. 3, represented by a 10 hour averaging or data smoothing, indicates high volatility in the change of HTR, which is shown in the top portion. The increased sensitivity of the inventive sensing units described above is apparent when it is recognized that units as small as $1.0 \times 10^{-5}$ are utilized to measure heat transfer resistance. Averaging of the changes in HTR over a number of hours tends to smooth the data. Good results were indicated for data smoothing over a range from 5 to 1000 hours.

As can be seen from the bottom portion of FIG. 3, the 10 hour data smoothing as shown therein does not provide a completely accurate indication of general trends in the increase of heat transfer resistance. For example, a spike 64 arising from unexplained or anomalous phenomena can severely skew the 10 hour average indicated by the lower portion in FIG. 3 and gives rise to a corresponding spike 66 in the curve 62. Under normal parameter monitoring, the magnitude of the spike 66 in curve 62 is of equal or even lesser importance than the onset of an actual increase in heat transfer resistance, as shown by the sloped rise 68 in curve 60, which is reflected by double spikes 70,72 in the curve 62. As can be seen from curve 62, the anomalous spike 66 could have triggered addition of an inhibiting agent whereas the actual rise in heat transfer resistance would not have done so.

FIG. 4 is a similar plot to that of the bottom portion of FIG. 3 with the exception that instead of 10 hour data smoothing (averaging), the data analysis provides for 50 hour data smoothing. The curve 74 accordingly begins the plot corresponding to hour 50 on the horizontal axis when there is a sufficient amount of data, over 90 hours, to begin the plot.

Again, the spike 64, occurring just after the hour 300, is reflected in a rise 76 in the curve 74. However, setting an arbitrary threshold value for the change in heat transfer resistance slope at $0.4 \times 10^{-6}$ $[(hr.\text{-}ft^2\text{-}°F.)/Btu]/hr.$, arbitrary threshold value for the change in heat transfer represented by dotted line 78, rise 76 is seen to not be high enough to surpass the threshold 78. On the other hand, rise 80, representing the increase in heat transfer resistance 68 (FIG. 3), surpasses the threshold 78 and provides an indication that an inhibiting agent should be added to the circulating water system. The 50 hour data smoothing curve 74 is also not completely precise as is apparent from the number of other data peaks which approach or reach the threshold limit 78, but which do not necessarily reflect a sustained increase in the rate of change in the heat transfer resistance.

FIG. 5 illustrates a third curve 82 which corresponds to a 100 hour data smoothing of the data used in the previous two curves 62,74. With greater times for the averaging of the data, the threshold limit, represented by dotted line 84, is lower, e.g. at $0.2 \times 10^{-6}$ $[(hr\text{-}ft^2\text{-}°F.)]/hr.$, with 100 hour data smoothing, the anomalous spike 64 drops out, but the rise 68 translates into a peak 86 clearly indicative of an increase in heat transfer resistance. Nevertheless, curve 82 smoothes out the remainder of the peaks to avoid the threshold 84 until a second significant increase in heat transfer resistance becomes obvious at peak 88.

FIG. 6 illustrates a curve 90, representing 200 hour data smoothing, which can also be used to indicate the need for addition of an inhibiting agent. However, at 200 hour data smoothing, the curve 90 is flattened to a great degree such that the information content and analysis begins to become negligible. Moreover, the threshold limit, represented by dotted line 92, must be set very low, e.g. $0.1 \times 10^{-6}$ $[(hr\text{-}ft^2\text{-}°F.)/Btu]/hr$, the slope of the curve 90 parallels the line 92 to some extent. The difference between a peak 94 and the rest of the line 92 becomes so small as to diminish its analytical value. Of course, data smoothing at periods exceeding 200 hours diminishes even more any meaning which may be derived from the data and also develops a significant lag time (over 200 hours) between commencement of data gathering of the heat transfer resistance and the time when data on the slope is provided.

FIG. 7 is a cutaway view of a circulating water system condenser tube 100 illustrating another embodiment of the present invention. An advantage of this embodiment of the sensing unit 102 is the elimination of a sidestream test tube since the sensing unit is disposed directly in the mainstream tubes 100 of the circulating water system.

Referring now to FIGS. 7-9, FIGS. 8 and 9 being elevational views of the perspective view of FIG. 7, the alternative embodiment sensing unit 102 comprises a probe extension portion 104 and an outer ring structure 106 used for attaching the unit 102 within the tube 100. The probe extension portion 104 preferably has a diameter and a length which permits insertion into the end of a condenser tube 100, so that the probe extension portion 104 can provide readings of water temperature well within the tube 100. A length of approximately 8 inches has been found to be adequate for a ⅜ inch inner diameter condenser tube 100. The preferred probe extension portion 104 for a ⅞" diameter pipe is about 0.1/4" thick at the thickest part and about ⅝" wide, being rounded at an outer diameter surface 110 so as to fit and closely follow the contour of the inside diameter of the tube 100. At the inside diameter, a flat surface 112 extends along the majority of the longitudinal dimension of the probe extension portion 104.

A flat end surface 114 slopes upwardly from the flat inner diameter surface 114 and intersects the rounded surface 110 at an acute included angle which is preferably 10° or less. Upon insertion of the probe extension portion 104 into a condenser tube 100, the included angle defines the leading edge of the intersection of surfaces 110 and 114 for water flowing through the condenser tube 100 in the direction of the arrow. A smaller included angle would thus produce less drag on the water stream flowing through the tube 100. Accordingly, this construction of the probe extension portion 104 approximates the amount, speed and pressure of the water flowing through the tube 100 when the portion 104 is present to that which would arise should the portion 104 be removed.

The probe extension probe 104 is connected to, and extends through, an outer ring structure 106 which is in the shape of a short length of tubing having dimensions similar to the condenser tube 100. Preferably, the inner diameter of the ring structure 106 matches the inner diameter of the condenser tube so as to not affect the characteristics of the flow of water through the tube 100 and along the probe extension portion 104.

A hose clamp 120 (FIG. 7) couples the outer ring structure 106 to the end of the condenser tube 100, and consequently defines the position of the probe extension portion 104 within the tube 100. A fast drying epoxy may be used with known methods to cement the portion 104 to the inside of condenser tube 100 by using known methods.

An electrical cable leads 26, which are impervious to hot water at high temperatures, are connected to the end of the probe extension portion 104 which reaches to the opposite side of the outer ring structure 106 from the hose clamp 120. The cable leads 26 extend through a wall (not shown) that defines the container and vessel of the condenser and connects the sensing unit 102 to the deposit monitor 28 and CPU 30 (FIG. 1) similar to the connections made of sensing unit 16 by heads 36 (FIG. 1). The cable leads 26 may be glued, tacked or otherwise attached to the inside walls of the condenser (not shown) to maintain a clear space for water flow through tubes 100.

The above described embodiments are for purposes of illustration and description of the invention and it is understood that other embodiments and modifications will become readily apparent to persons of ordinary skill in the art. Accordingly, the above embodiments are described as examples only and do not limit the scope of the following claims.

We claim:

1. A method of correcting for scale former which is deposited on the inside walls of a water container through which water is flowing in a circulating water system at a predetermined temperature, the method comprising:

a. providing at least one sensing unit for sensing heat transfer rate or heat transfer resistance through a contact surface which is in contact with the water in said circulating water system;

b. providing a deposit monitor station for monitoring heat transfer rate or heat transfer resistance and further providing an electrical connection between said at least one sensing unit and said deposit monitor station;

c. providing at one area adjacent to said contact surface a first temperature modulator to maintain that area at a temperature which stimulates scale deposit of the scale former on said surface;

d. periodically monitoring said sensing unit by measuring at predetermined time intervals the heat transfer rate or heat transfer resistance being sensed by said sensing unit, generating an electrical signal corresponding to the heat transfer rate or heat transfer resistance being sensed and transmitting said electrical signal to said deposit monitor station, said monitor station including a set of predetermined parameters indicative of scale formation in said circulating water system;

e. recording the signal received by said deposit monitor station to produce an electrical signal record and analyzing said electrical signal record to determine whether said analyzed electrical signal record matches said predetermined parameters indicative of scale formation in said circulating water system;

f. upon matching of said analyzed electrical signal record to the predetermined parameters, said electrical signal record corresponding to the heat transfer rate, and indirectly to the rate of scale formation, calculating a dosage of scale inhibitor determined sufficient to inhibit further formation of scale deposit upon said contact surface; and g. imparting into the circulating water system the calculated dosage of scale inhibitor deemed sufficient to inhibit further formation of scale deposit on said surface as well as on the inside walls of said water container.

2. A method according to claim 1 wherein said scale deposit is of a scale former which has an inverse relationship between solubility and temperature, and the first temperature modulator comprises a heat generator for providing heat to the contact surface thereby increasing the rate of scale deposit formation.

3. A method according to claim 2 wherein said scale former comprises calcium carbonate.

4. A method according to claim 1 wherein said water container comprises a boiler, cooling tube, or part of a heat exchanger.

5. A method according to claim 1 wherein the step of imparting scale inhibitor further comprises providing a pump which receives an electrical signal corresponding to the calculated dosage of scale inhibitor, said pump having a controller to vary its pumping rate, said controller varying the pumping rate of the scale inhibitor being pumped directly into the circulating water system as a result of receiving said electrical signal.

6. A method according to claim 1 further comprising the steps of:

providing a second sensing unit for sensing heat transfer rate or heat transfer resistance through said contact surface at a temperature of the contact surface which is equivalent to the temperature of the circulating water system;

periodically monitoring said second sensing unit by measuring at predetermined time intervals the heat transfer rate or heat transfer resistance being sensed by said second sensing unit, generating a second electrical signal corresponding to the heat transfer rate or heat transfer resistance being sensed by said second sensing unit and transmitting said second electrical signal to said deposit monitoring station;

recording the second electrical signal received by said deposit monitor station and analyzing said second electrical signal record to determine whether said analyzed electrical signal matches said predetermined parameters indicative of scale formation in said circulating water system have been met;

comparing the analyzed electrical signals from both sensing units for a determination of the extent to which the predetermined parameters associated with each sensing unit match and adjusting said calculated scale inhibitor dosage in accordance therewith .

7. A method according to claim 1 wherein said contact surface comprises a surface of a probe extension portion being disposed directly within the water flowing through the circulating water system.

8. The method according to claim 1 further comprising the step of providing a conduit having a conduit wall which is connected in fluid communication with the circulating water system to permit a side stream continuous flow of the water through said conduit, the contact surface comprising the inside of said conduit wall, said at least one sensing unit being disposed on the outside of said conduit wall.

9. A method of correcting for scale deposit according to claim 1 wherein said step for analyzing said electrical signal record includes calculating the slope of change of heat transfer resistance through said contact surface and averaging the slope data for a period in excess of 5 hours and not in excess of 1000 hours to provide slope data.

10. The method according to claim 9 wherein the slope data is averaged for a period in excess of 50 hours and not in excess of 200 hours.

11. The method according to claim 1 where the step of providing said at least one sensing unit further comprises providing said unit within the water flowing through said circulating water system and also providing a means for extending through the walls of said water container then electrical connection between said at least one sensing unit and said deposit monitor station.

12. A method according to claim 12 in which the scale inhibitor is fed by a pump, said pump having a controller to vary its pumping rate, said controller being activated upon receiving an activating signal, and a means to generate an activating signal when said scale former being deposited on said surface, as determined at the measuring and analysis steps, exceeds said predetermined parameters.

13. A method of correcting for scale former which is deposited on the inside walls of a water container through which water is flowing at a predetermined temperature comprising:

a. connecting to the container a conduit for withdrawing a sample of the water, the conduit having a conduit wall;

b. attaching to the conduit wall a heat generator to maintain the skin temperature of the inside of the conduit wall at a temperature which stimulates scale deposit at the conduit wall immediately adjacent said generator;

c. operating the heat generator so as to maintain the temperature of the inside of the conduit wall at a temperature which stimulates scale deposit over a period of time in excess of five hours;

d. measuring over a period of time in excess of five hours the heat transfer through said conduit wall and monitoring the thickness of said scale deposit;

e. analyzing the measured heat transfer through said conduit wall and said scale deposit to determine whether the monitored scale thickness exceeds a set of predetermined parameters indicative of scale formation; and f. introducing into the container through which the water is flowing a dosage of scale inhibitor which, based upon the analysis of heat transfer through said conduit wall as measured in step d, is determined sufficient to inhibit further formation of scale deposit in said water.

14. A system for correcting scale former which is deposited on the inside walls of a water container through which water is flowing in a circulating water system at a predetermined temperature, the system comprising:

a. at least one sensing unit for sensing heat transfer rate or heat transfer resistance through a contact surface which is in contact with the water in said circulating water system;

b. a deposit monitor station for monitoring the heat transfer rate or heat transfer resistance through said contact surface by periodically measuring at predetermined time intervals the amount of heat transfer rate or heat transfer resistance being sensed by said sensing unit and generating an electrical data signal corresponding to the measured amounts;

c. an electrical connection between said at least one sensing unit and said deposit monitor station for providing communication therebetween and for transmitting said electrical data signal corresponding to the heat transfer rate or heat transfer resistance being sensed and transmitting said electrical data signal to said deposit monitor station;

d. a first temperature modulator to maintain one area adjacent to said contact surface at a temperature which stimulates scale deposit of the scale former on said contact surface;

e. a recording and processing means for recording the electrical data signal received by said deposit monitor station and analyzing said electrical data signal record to determine whether said analyzed electrical signal, corresponding to the heat transfer rate or the heat transfer resistance matches predetermined parameters indicative of scale formation in said circulating water system and for calculating a dosage of scale inhibitor determined sufficient to inhibit further formation of scale deposit upon said contact surface; and f. a means for imparting into the circulating water system the calculated dosage of scale inhibitor deemed sufficient to inhibit further formation of scale deposit on said contact surface as well as on the inside walls of said water container.

15. A system according to claim 14 wherein said scale deposit is of a scale former which has an inverse relationship between solubility and temperature, and the first temperature modulator comprises a heat generator for providing heat to the contact surface thereby stimulating the formation of scale deposit.

16. A system according to claim 15 wherein said scale former comprises calcium carbonate and the means for imparting into the circulating water system further comprises a product feed pump for imparting a scale inhibitor in a dosage, calculated by said processing means, to inhibit the further formation of calcium carbonate deposit.

17. A system according to claim 14 wherein said water container is chosen from the group consisting of boilers, cooling tubes, heat exchangers, and water transfer pipes.

18. A system according to claim 14 wherein the means for imparting scale inhibitor further comprises a pump which receives an activating electrical signal corresponding to the calculated dosage of scale inhibitor, said pump having a controller to vary its pumping rate, said controller varying the pumping rate of the scale inhibitor being pumped directly into the circulating water system as a result of receiving said activating electrical signal.

19. A system according to claim 14 further comprising a second sensing unit for sensing heat transfer rate or heat transfer resistance through said contact surface at a temperature of the contact surface which is equivalent to the temperature of the circulating water system and for generating a second electrical data signal corresponding thereto; and an electrical connection between said second sensing unit and said deposit monitor station for providing communication therebetween and for transmitting said second electrical data signal corresponding to the heat transfer rate or heat transfer resistance being sensed by said second sensing unit and transmitting said second electrical data signal to said deposit monitor station.

20. The system according to claim 14 wherein said at least one sensing unit further comprises a probe extension for insertion within a condenser tube of a mainstream of the circulating water system, and the electrical connection extends from said probe extension external of said condenser tube.

21. A system for correcting for scale former which is deposited on the inside walls of a water container containing a circulating water system through which water is circulating at a predetermined temperature, the system comprising:

a. at least one sensing unit for sensing heat transfer rate or heat transfer resistance through a contact surface which is in contact with the water in said circulating water system, said sensing unit for generating a data signal corresponding to the heat transfer rate or heat transfer resistance of the contact surface;

b. a deposit monitor station for monitoring the data signal corresponding to the heat transfer rate or heat transfer resistance and an electrical connection between said at least one sensing unit and said deposit monitor station;

c. a first temperature modulator disposed adjacent to said contact surface for maintaining the contact surface at a temperature which stimulates scale deposit of the scale former on said contact surface;

d. a recording means for recording the data signal received by said deposit monitor station, thereby generating a data signal record;

e. an analysis means for analyzing said data signal record to determine whether the analyzed data signal record, corresponding to the heat transfer rate or heat transfer resistance, matches predetermined parameters indicative of scale formation in said circulating water system and for calculating a dosage of scale inhibitor determined sufficient to inhibit further formation of scale deposit upon said surface; and f. an activation means for transmitting an activation signal which causes imparting into the circulating water system a dosage of scale inhibitor calculated to inhibit further formation of scale deposit on said surface as well as on the inside walls of said water container.

22. A system according to claim 21 wherein said water container further comprises a boiler, cooling tube, or part of a heat exchanger or transfer piping, in which said condition comprises scaling deposit formed on said conduit of a scale former having a solubility which is inversely proportional to temperature, said correcting agent being a scale inhibitor for inhibiting the formation of said scale deposit.

23. A system according to claim 21 in which the scale inhibitor is fed by a pump, said pump having a controller to vary its pumping rate, said controller being activated upon receiving an activating signal, and a computer to generate an activating signal when said scale former being deposited on said surface, as determined by the analysis means, exceeds said predetermined parameters.

24. The system according to claim 21 wherein said at least one sensing unit further comprises a probe extension for insertion within a condenser tube of a mainstream of the circulating water system, and the electrical connection extends from said probe extension external of said condenser tube.

* * * * *